(12) United States Patent
Hara

(10) Patent No.: US 12,076,179 B2
(45) Date of Patent: Sep. 3, 2024

(54) RADIATION DEVICE, RADIOGRAPHY DEVICE, CONSOLE, AND RECORDING MEDIUM

(71) Applicant: Konica Minolta, Inc., Tokyo (JP)

(72) Inventor: Kentaro Hara, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 252 days.

(21) Appl. No.: 17/846,568

(22) Filed: Jun. 22, 2022

(65) Prior Publication Data

US 2022/0401053 A1     Dec. 22, 2022

(30) Foreign Application Priority Data

Jun. 22, 2021   (JP) ................. 2021-103357

(51) Int. Cl.
   *A61B 6/00*     (2024.01)
   *A61B 6/46*     (2024.01)
   *A61G 3/00*     (2006.01)

(52) U.S. Cl.
   CPC .............. *A61B 6/54* (2013.01); *A61B 6/4405* (2013.01); *A61B 6/461* (2013.01); *A61B 6/56* (2013.01); *A61G 3/001* (2013.01)

(58) Field of Classification Search
   CPC ......... A61B 6/54; A61B 6/4405; A61B 6/461; A61B 6/56; A61B 6/542; A61G 3/001
   See application file for complete search history.

(56) References Cited

U.S. PATENT DOCUMENTS

2019/0290237 A1*   9/2019   Kuwata ................. A61B 6/548

FOREIGN PATENT DOCUMENTS

JP         5597055 B2    10/2014

\* cited by examiner

*Primary Examiner* — Courtney D Thomas
(74) *Attorney, Agent, or Firm* — CANTOR COLBURN LLP

(57) ABSTRACT

A radiation device is wirelessly connected to a radiography device that generates dynamic image data and which controls sequential radiation. The radiation device includes a signal generator and a first determiner. The signal generator generates (i) first pulse signals emitted by the radiography device, (ii) second pulse signals synchronized with a first count value obtained by counting up the first pulse signals, and (iii) a second count value obtained by counting up the second pulse signals. The first determiner determines whether to start radiation based on a delay time which is a difference between a first time point count value and a second time point count value. The first time point count value indicates a time point at which a radiation permission signal is transmitted. The second time point count value indicates a time point at which the radiation permission signal is received.

13 Claims, 10 Drawing Sheets

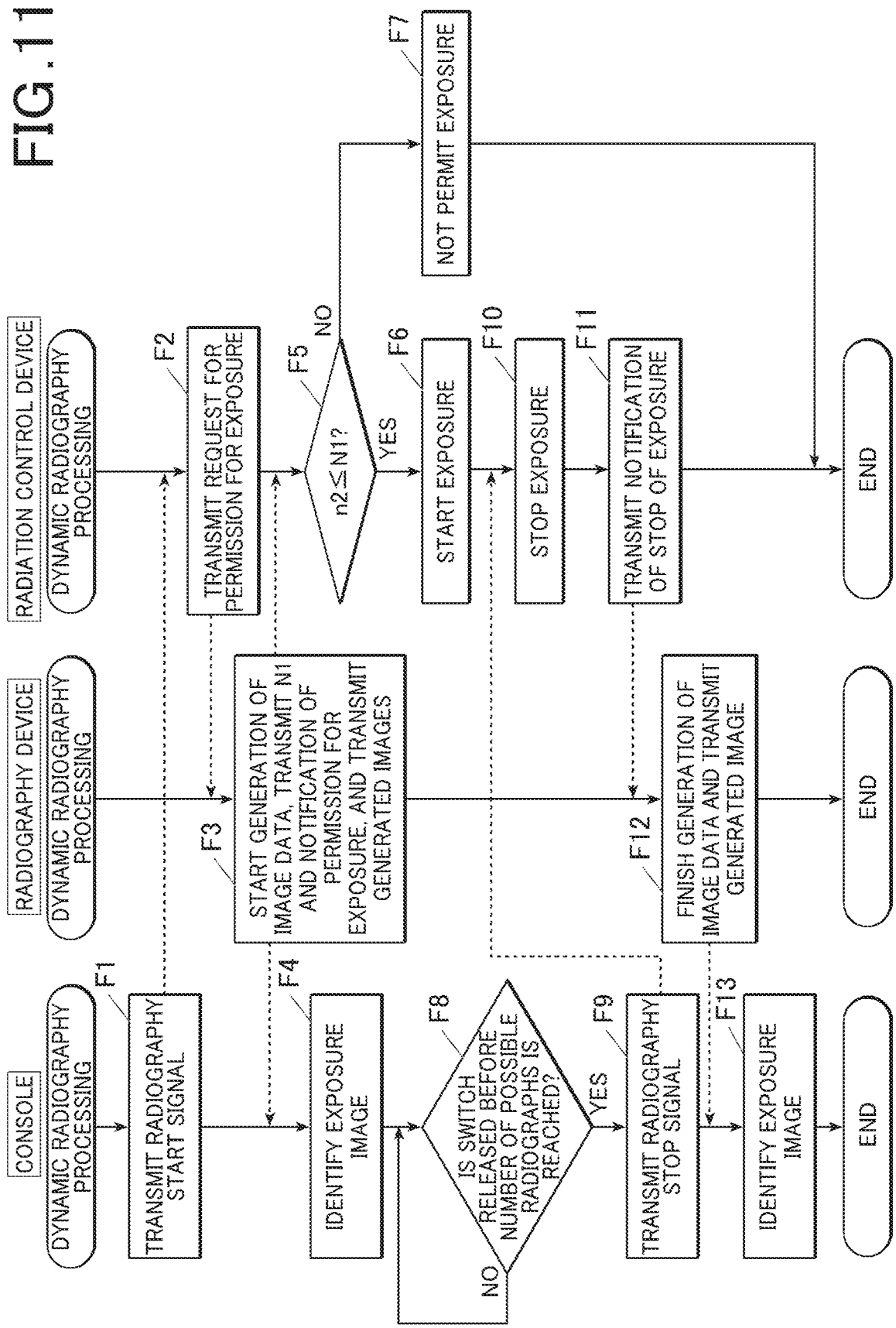

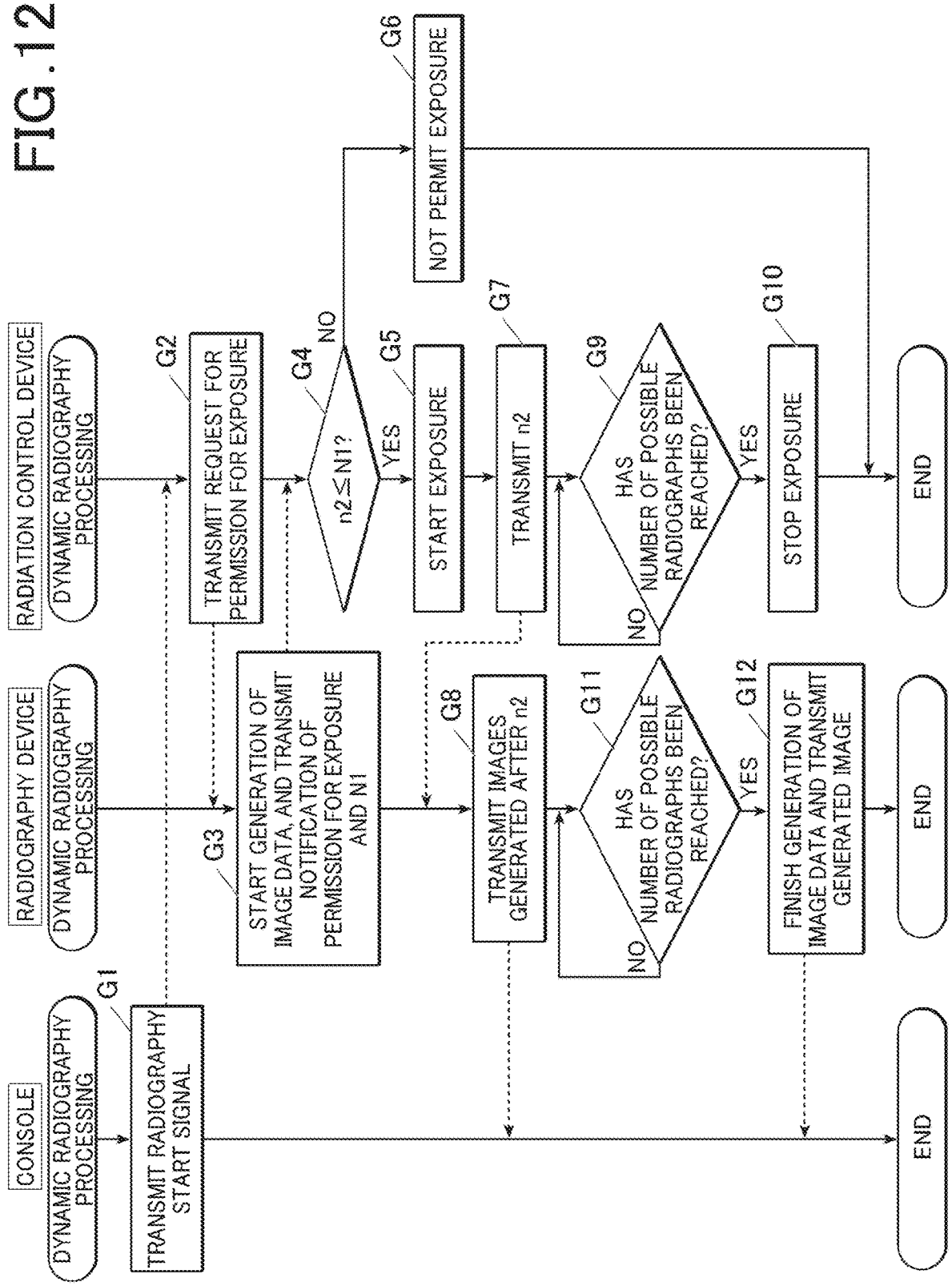

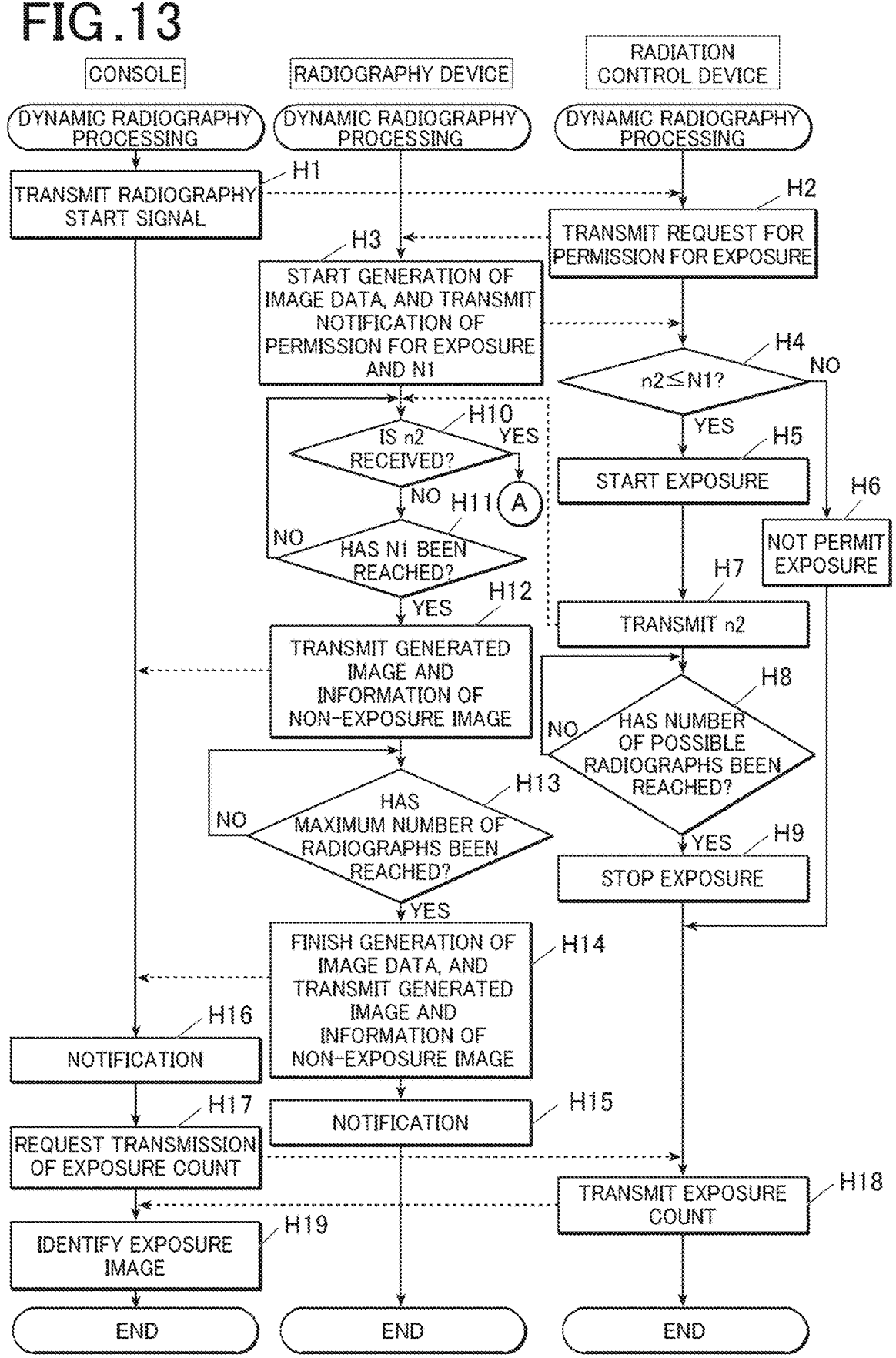

RADIATION DEVICE, RADIOGRAPHY DEVICE, CONSOLE, AND RECORDING MEDIUM

CROSS REFERENCES TO RELATED APPLICATIONS

The present invention claims priority under 35 U.S.C. § 119 to Japanese Application, 2021-103357, filed on Jun. 22, 2021, the entire contents of which being incorporated herein by reference.

BACKGROUND

1. Technological Field

The present invention relates to a radiation device, a radiography device, a console, and recording medium.

2. Description of the Related Art

Conventional radiography systems include:
a radiation device that generates radiation; and
a radiography device that generates image data of a radiation image based on received radiation.
Radiography systems continuously take images of a subject at regular intervals to obtain multiple frame images. Dynamic behavior (dynamics) of the subject is analyzed by this dynamic radiography for a diagnosis.
Dynamic radiography can cause a gap (delay time to start radiation exposure) between:
time at which a signal indicating radiation exposure is input to the radiation device; and
time at which radiation exposure is initiated by the radiation device in response to the input.
Dynamic radiography can also cause a gap (delay time to stop radiation exposure) between:
time at which a signal indicating an end of radiation exposure is input to the radiation device; and
time at which radiation exposure by the radiation device ends in response to the input.
The delay time can affect image quality of images to be taken.
In this regard, the control device described in Japanese Patent No. 5597055 measures:
a delay time between input of a signal indicating X-ray exposure and actual exposure of X-ray; and
a delay time between input of a signal indicating an end of X-ray exposure and an actual end of X-ray exposure.
The control device controls X-ray exposure based on the delay time.
Radiography systems in which a radiation device and a radiography device are wirelessly connected and operate in synchronization with each other may cause:
a delay time for notification of permission for exposure between a time point at which the radiography device starts generating images and a time point at which the radiation device starts exposing radiation; and
a delay time for notification of stop of exposure between a time point at which the radiation device stops exposing radiation and a time point at which the radiography device finishes generating images.
Since the radiation device and the radiography device are wirelessly connected, the delay time for notification of permission for exposure and the delay time for notification of stop of exposure are unstable depending on the communication environment.

In some cases, especially when the delay time for notification of permission for exposure is long, the planned number of frames of dynamic radiography cannot be performed. It is not possible to perform dynamic radiography suitably.
Japanese patent No. 5597055 does not disclose the delay time for notification of permission for exposure and the delay time for notification of stop of exposure in the control device. The control device cannot solve the above problems.

SUMMARY

The present invention was made in view of the above problems. The purpose of the present invention is to enable dynamic radiography that generates multiple frame images to be performed more suitably even when a radiation device that generates radiation and a radiography device that generates radiation images are wirelessly connected.
To achieve at least one of the above-mentioned objects, according to an aspect of the present invention, a radiation device is wirelessly connected to a radiography device that generates dynamic image data and controls sequential radiation to a subject, the radiation device comprising:
a signal generator; and
a first determiner,
wherein
the signal generator generates:
first pulse signals emitted by the radiography device,
second pulse signals synchronized with a first count value obtained by counting up the first pulse signals; and
a second count value obtained by counting up the second pulse signals, and
the first determiner determines whether to start radiation based on a delay time which is a difference between:
a first time point count value indicating a time point at which a radiation permission signal is transmitted, the radiation permission signal being wirelessly transmitted from the radiography device to allow the radiation device to start radiation; and
a second time point count value indicating a time point at which the radiation permission signal is received.
According to another aspect of the present invention, a radiography device generates dynamic image data and is wirelessly connected to a radiation device that controls sequential radiation to a subject, the radiography device comprising:
a second determiner that determines whether information on a time point at which the radiation device starts radiation is received within a predetermined period; and
a third transmitter,
wherein
in a case where the second determiner determines that the information on the time point at which radiation is started is received within the predetermined period, the third transmitter transmits, to a predetermined external device, the dynamic image data generated after the time point at which radiation is started, and
in a case where the second determiner determines that the information on the time point at which radiation is started is not received within the predetermined period, the third transmitter transmits, to a predetermined external device,
the dynamic image data generated after a time point at which generation of the dynamic image data is started; and information that the dynamic image data includes non-exposure image data.

According to still another aspect of the present invention, a console is configured to be connected with the radiation device, the console including:
- a second identification unit that identifies exposure image data generated under radiation among pieces of the dynamic image data based on increase/decrease or shape of signal values in the dynamic image data transmitted from the radiography device.

According to still another aspect of the present invention, a non-transitory computer-readable recording medium stores a program for a computer of a radiation device, wherein:
- the radiation device controls sequential radiation to a subject and is wirelessly connected to a radiography device that generates dynamic image data,
- the program makes the computer function as:
  - a signal generator; and
  - a first determiner,
- the signal generator generates:
  - first pulse signals emitted by the radiography device,
  - second pulse signals synchronized with a first count value obtained by counting up the first pulse signals; and
  - a second count value obtained by counting up the second pulse signals, and
- the first determiner determines whether to start radiation based on a delay time which is a difference between:
  - a first time point count value indicating a time point at which a radiation permission signal is transmitted, the radiation permission signal being wirelessly transmitted from the radiography device to allow the radiation device to start radiation; and
  - a second time point count value indicating a time point at which the radiation permission signal is received.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 11 is a flowchart showing dynamic radiography processing of Modification 4.

FIG. 12 is a flowchart showing dynamic radiography processing of Modification 5.

FIG. 13 is a flowchart showing dynamic radiography processing of Modification 6.

DESCRIPTION OF EMBODIMENTS

Figure 1:
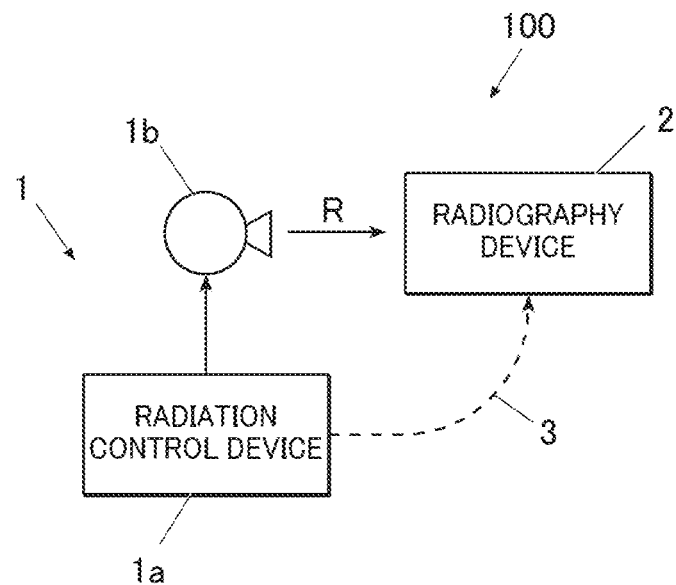
FIG. 1 is a block diagram showing a radiography system according to an embodiment of the present invention.

Embodiments of the invention will be described with reference to the drawings. The scope of the claims of the invention is not limited to examples illustrated in the drawings.

1. Radiography System

First, a schematic configuration of a radiography system (radiography system 100) according to the embodiment will be described. FIG. 1 is a block diagram showing a schematic configuration of the radiography system 100.

1-1. Schematic Configuration of Radiography System

As shown in FIG. 1, the radiography system 100 of the present embodiment includes:
- a radiation device 1;
- one or more radiography devices 2; and
- an external interface.

Radiation Device

The radiation device 1 generates radiation R (e.g., X-ray) to irradiate a subject and the radiography device 2 behind the subject with the radiation R. The radiation device 1 includes a radiation control device 1a and a tube 1b.

The specific configuration of the control device 1a will be described below.

Radiography Device

The radiography device 2 receives radiation R from the radiation device 1 to generate image data. The radiography device 2 can communicate with the radiation device 1.

The specific configuration of the radiography device 2 will also be described below.

External Interface

The external interface connects, for example, the radiation device 1 and the radiography device 2 for communication.

For example, the external interface includes:
- a communication cable 3;
- a cradle into which the radiography device 2 is plugged; and
- a housing 7 in a medical vehicle (described below) which houses the radiography device 2.

The external interface can be disconnected (e.g., unplugged) from at least one of the radiation device 1 and the radiography device 2, if necessary.

1-2. Schematic Operation of Radiography System

In the radiography system 100 of the embodiment with such a configuration, the radiation device 1 irradiates, with radiation R, a subject disposed between the radiation device 1 and the radiography device 2 to radiograph the subject.

The radiography system 100 of the embodiment can shoot videos (hereafter referred to as "dynamic radiography"). In response to one radiography operation (pressing of an exposure switch 6a which will be described below), the radiation device 1 generates pulsed radiation R of a preset time width a plurality of times in succession at regular intervals. The radiography device 2 generates frame images that constitute a video. Dynamic radiography includes video recording but does not include taking still pictures while displaying a video. A series of images obtained by dynamic radiography is called a dynamic image. Dynamic images include videos, but do not include images obtained by taking still pictures while displaying a video.

The radiography system 100 may communicate with other systems, such as a radiology information system (RIS) or a picture archiving and communication system (PACS), and an analysis device.

2. Radiation Device

Figure 2:
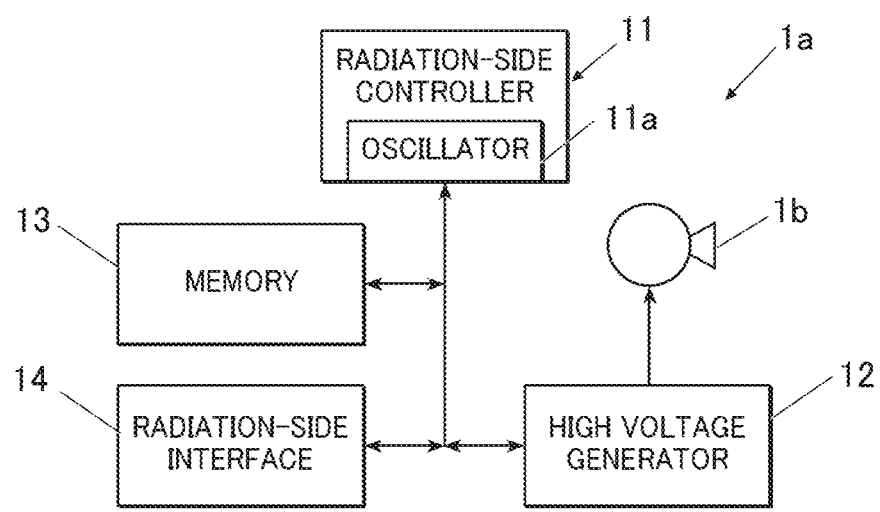
FIG. 2 is a block diagram showing a specific configuration of a radiation device provided in the radiography system of FIG. 1.

Next, details of the control device 1*a* provided in the radiation device 1 will be described. FIG. 2 is a block diagram showing a specific configuration of the control device 1*a*.

2-1. Specific Configuration of Radiation Device

As shown in FIG. 2, the control device 1*a* is constituted by a radiation-side controller 11, a high voltage generator 12, memory 13, a radiation-side interface 14, and the like.

These components 11-14 of the control device 1*a* are powered by a power cable or a built-in power supply (not shown).

The radiation-side controller 11 includes a CPU (central processing unit) and RAM (random access memory) (not shown). The radiation-side controller 11 comprehensively controls operation of the components 12-14 of the radiation device 1.

The radiation-side controller 11 includes an oscillator (radiation-side oscillator 11*a*). The radiation-side oscillator 11*a* may be constituted by a crystal oscillator, a ceramic oscillator, or the like that generates a clock of a predetermined period when the device is turned on.

The radiation-side controller 11 has a function of periodically generating timekeeping information using a clock generated by the radiation-side oscillator 11*a*. The timekeeping information generated here includes, for example, a time point signal (second pulse signals) and time information. The time point signal is pulse signals or the like that are output when one or more clocks are generated. The time information is a count value (second count value) obtained by counting up the second pulse signals, etc.

The components 11-14 of the radiation device 1 operate based on a clock generated by the radiation-side oscillator 11*a*.

The radiation-side oscillator 11*a* may be a plurality of oscillators that are used for different purposes, such as required accuracy.

The radiation-side controller 11 synchronizes the time point signals and count values with those of the radiography device 2 by executing synchronization processing described below.

That is, the radiation-side controller 11 generates:
the first pulse signals (see below) emitted by the radiography device 2;
the second pulse signals synchronized with the first count value (see below) obtained by counting up the first pulse signals; and
the second count value obtained by counting up the second pulse signals.

Thus, the radiation-side controller 11 functions as a signal generator.

The radiation-side controller 11 executes the dynamic radiography processing described below.

Thereby, the radiation-side controller 11 determines whether to start radiation based on a delay time which is the difference between:
the first time point count value indicating a time point of transmission of a radiation permission signal that is wirelessly transmitted from the radiography device (radiography device 2) to allow the radiation device (radiation device 1) to start radiation; and
the second time point count value indicating a time point at which the radiation permission signal is received.

Thus, the radiation-side controller 11 functions as the first determiner.

The radiation-side controller 11 executes the dynamic radiography processing described below. Thereby, the radiation-side controller 11 transmits, to a predetermined external device, information on a time point at which radiation is started. Thus, the radiation-side controller 11 functions as the first transmitter.

The high voltage generator 12 applies a voltage to the tube 1*b* in accordance with preset radiography conditions in response to receipt of a time point signal from the radiation-side controller 11.

For example, the radiography conditions are:
conditions related to a subject, such as an radiography mode (still or dynamic radiography), a part of a body to be radiographed, a body size; and
conditions related to irradiation of radiation R, such as a tube voltage, a tube current, a radiation time, and a current-time product.

The radiography mode included in the radiography conditions is information on a radiography method, such as still radiography or dynamic radiography. The radiography system 100 allows a user to set the radiography mode in advance, and the high voltage generator 12 operates in accordance with the setting of the radiography mode in a manner appropriate for the radiography mode.

In a case where the radiography conditions include dynamic radiography, the radiography system 100 repeatedly applies pulsed voltages at predetermined intervals every time a time point signal is received.

When a voltage is applied from the high voltage generator 12, the tube 1*b* generates radiation R with a dose corresponding to the applied voltage. Specifically, the tube 1*b* radiates pulsed radiation R in response to pulsed voltages applied by the high voltage generator 12.

The memory 13 is constituted by a HDD (hard disk drive), semiconductor memory, or the like. The memory 13 stores various processing programs as well as parameters and files necessary for executing the programs.

The memory 13 stores various data generated in processing by the radiation-side controller 11, such as timekeeping information.

The radiation-side interface 14 can be connected to an external interface and can transmit and receive information of various types (signals and data).

Specifically, the radiation-side interface 14 may consist of a connector or the like into which the communication cable 3 is plugged.

2-2. Specific Operation of Radiation Device

The radiation-side controller 11 of the radiation device 1 thus configured operates as follows according to programs stored in the memory 13.

For example, the radiation-side controller 11 sets various radiography conditions including:
conditions related to a subject, such as an radiography mode (still or dynamic radiography), a part of a body to be radiographed, a body size; and
conditions related to radiation of radiation R, such as a tube voltage, a tube current, a radiation time, a current-time product, and a frame rate.

In response to receipt of the radiation permission signal, the radiation-side controller 11 controls the high voltage generator 12 to start exposure (radiation).

In a case where the radiography conditions include dynamic radiography, the radiation-side controller 11 performs exposure at a cycle corresponding to the frame rate.

3. Configuration of Radiography Device

Figure 3:
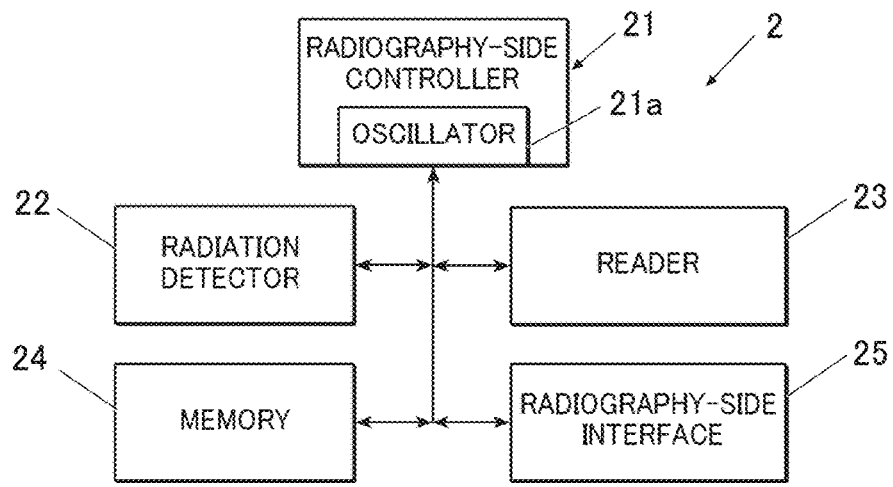
FIG. 3 is a block diagram showing a specific configuration of a radiography device provided in the radiography system of FIG. 1.

Next, a specific configuration of the radiography device 2 provided in the radiography system 100 will be described. FIG. 3 is a block diagram showing a specific configuration of the radiography device 2.

3-1. Specific Configuration of Radiography Device

As shown in FIG. 3, the radiography device 2 of the embodiment includes a radiography-side controller 21, a radiation detector 22, a reader 23, memory 24, a radiography-side interface 25 in addition to a case (not shown).

These components 21-25 of the radiography device 2 are powered by a power cable or a built-in power supply (not shown).

The radiography-side controller 21 comprehensively controls operation of the components 22-25 of the radiography device 2 with a CPU, RAM, etc.

The radiography-side controller 21 includes an oscillator (hereinafter referred to as radiography-side oscillator 21*a*). The radiography-side oscillator 21*a* may be constituted by a crystal oscillator, a ceramic oscillator, or the like that generates a clock of a predetermined period when the device is turned on.

The radiography-side controller 21 has a function of periodically generating timekeeping information using a clock generated by the radiography-side oscillator 21*a*. The generated timekeeping information includes, for example, a time point signal (first pulse signal) and time information. The time point signal is pulse signals or the like that are output when one or more clocks are generated. The time information is a count value (first count value), etc. obtained by counting up the first pulse signal. A format of the generated timekeeping information should preferably be adapted to timekeeping information generated by the radiation device 1.

The components 21-25 of the radiography device 2 operate based on the clock generated by the radiography-side oscillator 21*a*.

The radiography-side oscillator 21*a* may be a plurality of oscillators that can be used for different purposes, such as the required accuracy.

The radiography-side controller 21 executes dynamic radiography processing described below. Thereby, the radiography-side controller 21 identifies exposure image data generated under radiation among generated pieces of dynamic image data based on information on a time point at which radiation is started. At this time, the radiography-side controller 21 functions as the first identification unit.

The radiation detector 22 should have a substrate with a plurality of pixels arranged in a two-dimensional array.

The substrate includes:
- radiation detector elements that each generate, directly or indirectly, an electric charge corresponding to a dose of radiation R received from an external source; and
- a switch element provided between each radiation detector element and the wiring.

The switch element can switch between an on-state, in which energization between the radiation detector elements and the wiring is possible, and an off-state, in which energization is not possible. Conventional known items can be used for the radiation detector 22.

To be specific, the radiography device 2 may be:
- the so-called indirect type, which is equipped with a scintillator and detects light emitted by the scintillator when it is exposed to radiation R; and
- the so-called direct type, which directly detects radiation R without a scintillator, etc.

The reader 23 reads a signal value corresponding to an amount of charge accumulated in each of the radiation detector elements (generated by the radiation detector elements). The reader 23 generates image data of a radiation image based on signal values. Conventionally known items can be used for the reader 23.

The memory 24 is constituted by a HDD, semiconductor memory, etc. The memory 24 stores various processing programs as well as parameters and files necessary for executing the programs.

The memory 24 stores various data generated in processing by the radiography-side controller 21, such as timekeeping information.

The radiography-side interface 25 can be connected to an external interface and can transmit and receive information of various types (signals and data).

Specifically, the radiography-side interface 25 may consist of a connector or the like into which the communication cable 3 is plugged.

In a case where the radiography device 2 is powered by a built-in power supply, the built-in power supply can be a lithium ion capacitor (LiC), a lithium ion battery (LiB), or another power supply.

Lithium ion capacitors can be quickly recharged and do not ignite, so after completing radiography (e.g., moving radiography), the next radiography can be performed in a short time.

On the other hand, lithium-ion batteries are inexpensive and have a large capacity, which can lower the manufacturing cost of the radiography device 2 and reduce the number of times it needs to be recharged.

Either configuration is preferable for performing radiography multiple times.

3-2. Specific Operation of Radiography Device

The radiography-side controller 21 of the radiography device 2 thus configured operates as follows according to programs stored in the memory 24.

For example, the radiography-side controller 21 has a function of switching a state of the radiography device 2 to one of an "initialization state", an "accumulation state", and a "read/transfer state".

The "initialization state" is a state in which an on-voltage is applied to each switch element and a charge generated by the radiation detector is not stored in each pixel (charge is released to a signal line).

The "storage state" is a state in which an off-voltage is applied to each switch element and a charge generated by the radiation detector can be stored in each pixel (charge is not released to the signal line).

The "read/transfer state" is a state in which an on-voltage is applied to each switch element and the reader 23 is driven to read signal values based on an incoming charge.

Repetition of operation of returning to the initialization state before performing dynamic radiography consumes a lot of power.

Therefore, the radiography device 2 may start repeating the operation of returning to the initialization state before dynamic radiography in response to predetermined operation by a user. Alternatively, the radiography device 2 may set a time equivalent to a working process as WAIT and may start automatically after WAIT has elapsed.

In this way, power consumption can be reduced in a series of working processes.

4. Mobile Radiography System

Figure 4:
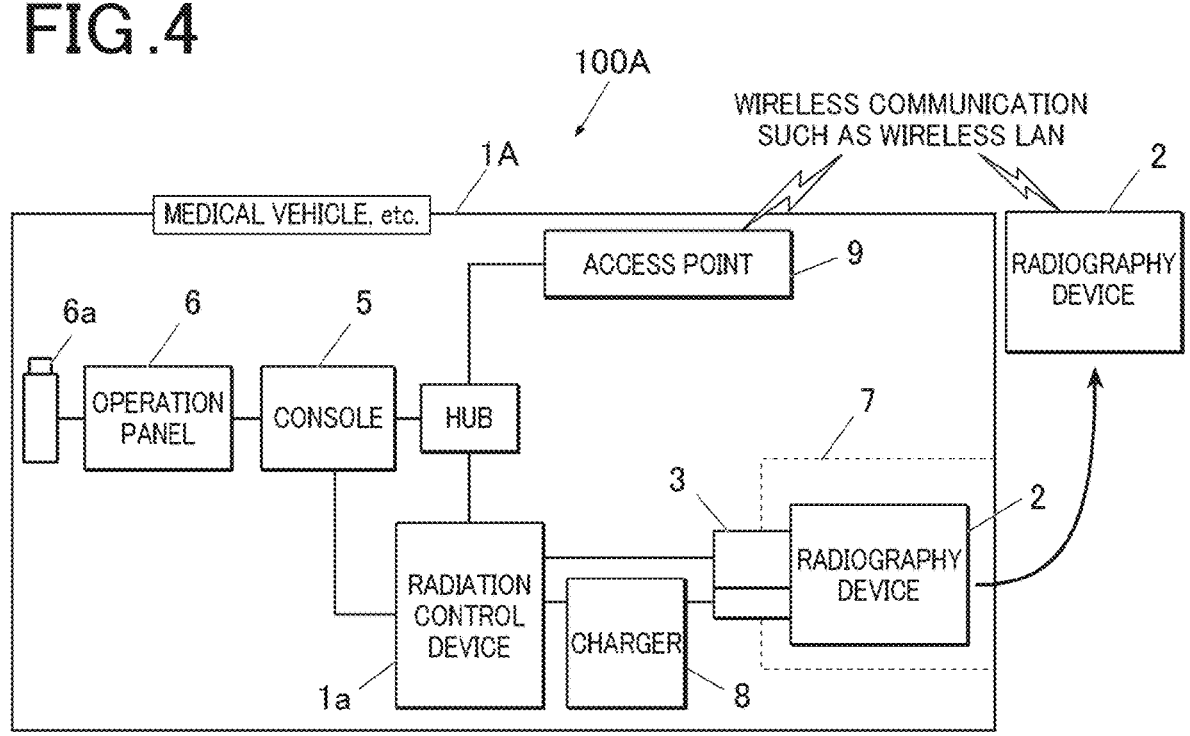
FIG. 4 is a block diagram showing an example of a mobile radiography system configured with the radiography system of FIG. 1.

Next, details of a mobile radiography system 100A in which the radiography system 100 is used will be described. FIG. 4 is a block diagram showing an example of the mobile radiography system 100A.

4-1. Background

To perform radiography using a radiography table installed in a radiography room of a hospital, a communication cable and a power cable are connected to the radiography device 2 installed on the table.

Information is sent and received between the radiography device 2 and the radiation device 1, and power is supplied to the radiography device 2.

For example, when a communication cable is used for connection with the radiography device 2, it is possible to synchronize the radiation device 1 with the radiography device 2 for radiography by including pulse signals or a time point signal in control signals of the communication cable.

However, there are cases where, for example, radiography must be performed in a radiography room with a patient in a wheelchair or on a bed.

In such cases, radiography with the communication cable still connected to the radiography device 2 causes problems such as:
- a problem that the communication cable gets in the way;
- a problem that there is a risk that the communication cable will come loose, and communication will be lost; and
- a problem that the communication cable touches a subject to cause unsanitary environment.

Therefore, it has been desired to perform radiography without a communication cable.

On the other hand, in a case where radiography is performed while moving with the mobile radiography system 100A, radiography is performed in a ward where a subject stays. In this case, radiography is performed in a bed on which the subject is lying. The radiography device 2 is taken out of the housing 7. The radiography device 2 is placed between the subject and the bed, and radiography is performed.

Compared with the above radiography in the radiography room, this radiography is more likely to cause problems such as:
- the problem that the communication cable gets in the way;
- the problem that there is a risk that the communication cable will come loose, and communication will be lost; and
- the problem that the communication cable touches a subject to cause unsanitary environment.

Therefore, it has been desired to perform radiography without a communication cable.

In radiography using computed radiography (CR), no communication cable is required. It has been also desired to perform radiography using the radiography device 2 without a communication cable in order to obtain the same ease of operation as in CR.

The radiography system 100 of the present embodiment which has the above-described configuration can also be used as the mobile radiography system 100A. Of course, it is also possible to install and use the radiography system 100 in a radiography room of a hospital, etc.

4-2. Specific Configuration of Mobile Radiography System

As shown in FIG. 4, the mobile radiography system 100A includes a medical vehicle 1A and the radiography device 2. The tube 1b is not shown in FIG. 4.

In addition to the control device 1a, the medical vehicle 1A includes a console 5, an operation panel 6, the housing 7, a charger 8, an access point 9, and wheels not shown. The medical vehicle 1A is movable.

The console 5 can set radiography conditions for at least one of the control devices 1a and the radiography device 2 based on:
- radiography orders obtained from other systems (HIS, RIS, etc.); or
- operation on the control panel 6 by a user (e.g., radiologist).

The radiography conditions include a radiography mode (still radiography or dynamic radiography), a tube voltage, a product of a tube current and a radiation time or a current time (mAs value), a portion to be radiographed, and a radiography direction.

The console 5 acquires image data of radiographic images generated by the radiography device 2. The console 5 stores it in itself and transmits it to other devices, such as a PACS and a dynamic analysis device.

The console 5 executes the dynamic radiography processing described below to identify exposure image data generated under radiation among pieces of dynamic image data based on increase/decrease or shape of signal values in the dynamic image data transmitted from the radiography system 2. Thus, the console 5 functions as the second identification unit.

The control panel 6 includes an exposure switch 6a.

In response to pressing of the exposure switch 6a, the console 5 sends a radiography start signal to the control device 1a. Thus, pressing the exposure switch 6a is operation to start exposure. In response to release of the exposure switch 6a, the console 5 sends a radiography stop signal to the control device 1a. Thus, release of the exposure switch 6a is operation to stop exposure.

The housing 7 is configured to be able to store the radiography device 2.

The housing 7 includes an external interface that is connected to the radiography-side interface 25 when the radiography device 2 is stored. Specifically, a tip of the communication cable 3 is attached to a point which is inside the housing 7 and which is opposite the radiography-side interface 25.

The charger 8 charges the built-in power supply of the radiography device 2.

The charger 8 may be:
- a charger that charges the built-in power supply by receiving power supply from an external power source (e.g., an outlet in hospital);
- a charger that charges the built-in power supply by receiving power supply from a power source in the medical vehicle 1A; and
- a charger that charges the built-in power supply with its own power source.

The access point 9 communicates wirelessly with the radiography device 2 using a wireless LAN (local area network), etc.

5. Dynamic Radiography Using Mobile Radiography System

5-1. Dynamic Radiography Operation

Figure 5:
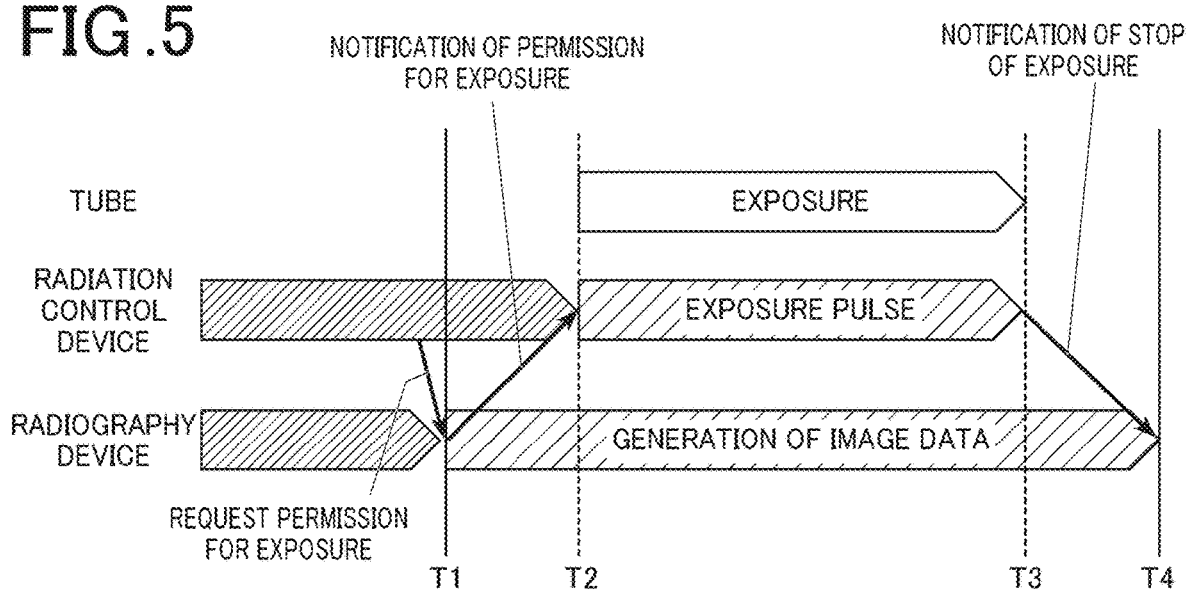
FIG. 5 shows an example of dynamic radiography in the mobile radiography system.

Next, the dynamic radiography operation performed by the mobile radiography system 100A shown in FIG. 5 will be described.

First, a user presses down the exposure switch 6a, which is operation to start exposure, in the mobile radiography system 100A. An exposure permission request is sent to the radiography device 2 from the control device 1a. Generation of image data is started in the radiography device 2. This time point is T1.

Next, notification of permission for exposure, which is the radiation permission signal, is sent to the control device 1a from the radiography device 2. The control device 1a starts exposure. This time point is T2.

The time between T1 and T2 is the delay time for notification of permission for exposure. During the delay time for notification of permission for exposure, non-exposure image data is generated. The non-exposure image data is image data generated in the absence of exposure.

After that, the user releases the exposure switch 6a, which is the operation to stop exposure, before the user finishes the number of possible radiographs, which is the maximum number of radiographs the user can get. The control device 1a stops exposure and sends notification of stop of exposure, which is a radiation stop signal, to the radiography device 2. This time point is T3.

Next, the radiography device 2 stops generating image data based on the received notification of stop of exposure. This time point is T4.

The time between T3 and T4 is the delay time for notification of stop of exposure. During the delay time for notification of stop of exposure, non-exposure image data is generated.

The number of pieces of image data that can be generated by the mobile radiography system 100A has an upper limit due to design constraints. Design constraints include a storage area of the memory 24 of the radiography device 2 and noise effects over time. If the number of pieces of image data that can be generated reaches the upper limit and exposure is performed while image data cannot be generated, exposure is wasted. To prevent unnecessary exposure, the sum of the number of possible radiographs and the number of pieces of non-exposure image data generated during the delay time for notification of permission for exposure must be less than or equal to the maximum number of radiographs. The maximum number of radiographs is the maximum number of pieces of generated image data due to design constraints.

As diagnostic images for use in diagnosis, only exposure image data generated under radiation should be obtained. In a dynamic analysis device that analyzes dynamic images, it is necessary to acquire only exposure image data in order to correctly analyze dynamic images. Therefore, it is necessary to identify exposure image data from pieces of image data generated by the radiography device 2.

To realize the above requirements, processing shown in FIG. 6 to FIG. 13 is executed in the mobile radiography system 100A.

5-2. Synchronization Processing

First, a user performs operation that triggers start of timekeeping by the radiation-side controller 11 of the radiation device 1a and the radiography-side controller 21 of the radiography device 2. For example, the user turns on devices of the mobile radiography system 100. Then, the radiation-side controller 11 and the radiography-side controller 21 start timekeeping respectively. If the devices are turned on at different times, time points to start timekeeping by the radiation-side controller 11 and the radiography-side controller 21 will be different. A time point at which the control device 1a generates timekeeping information and a time point at which the radiography device 2 generates timekeeping information are different at this stage.

Figure 6:
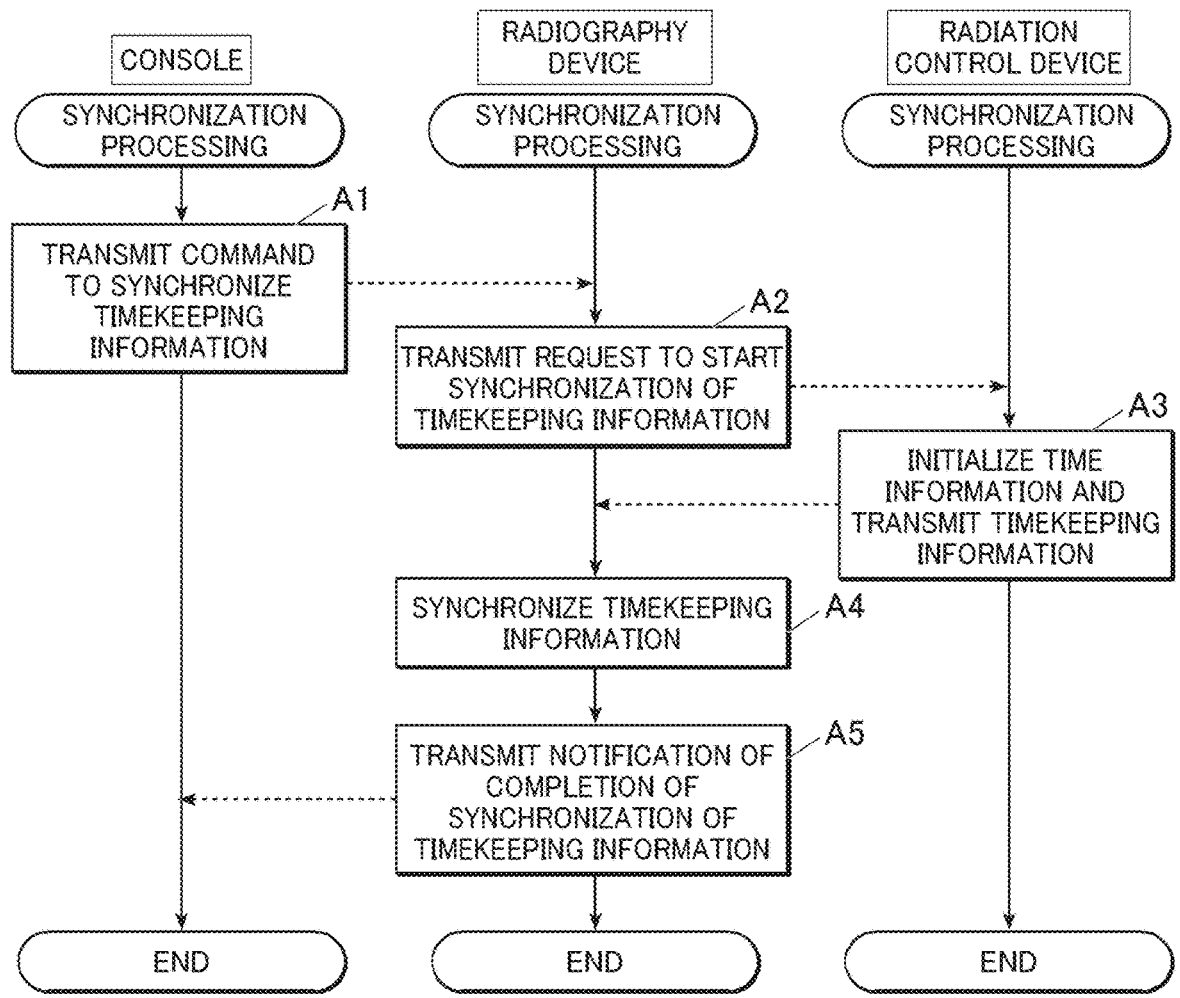
FIG. 6 is a flowchart showing synchronization processing.

The radiography device 2 is stored in the housing 7, and the radiation-side interface 14 of the control device 1a is connected to the radiography-side interface 25 of the radiography device 2. The synchronization processing shown in FIG. 6 is started in the control device 1a, the radiography device 2, and the console 5.

In the synchronization processing, first, the console 5 transmits to the radiography device 2, a command to synchronize timekeeping information (Step A1).

Next, the radiography-side controller 21 receives the command to synchronize timekeeping information and transmits, to the control device 1a, a request to start synchronization of timekeeping information (Step A2).

The radiation-side controller 11 receives the request to start synchronization of timekeeping information, initializes the count value that is time information, and transmits the generated timekeeping information to the radiography device 2 (Step A3).

The radiography-side controller 21 receives the timekeeping information and, based on the received timekeeping information, synchronizes its own timekeeping information at the time of receipt of the timekeeping information (Step A4). Specifically, based on a time point signal transmitted by the control device 1a, the radiography-side controller 21 generates a copy signal whose rising edge matches the time point signal. The radiography-side controller 21 synchronizes the count values.

The copy signal may originate at the falling point or may contain an error within required accuracy.

Thus, the radiation-side controller 11 and the radiography-side controller 21 generate timekeeping information with a common count value at one time point.

Next, the radiography-side controller 21 transmits to the console 5, notification of completion of synchronization of timekeeping information (Step A5).

The console 5 receives the notification of completion of synchronization of timekeeping information and finishes processing.

The user then disconnects the radiation-side interface 14 from the radiography-side interface 25 (i.e., the user moves the radiography device 2 to a radiography position). The radiography device 2 performs its own timekeeping. At this time, the timekeeping information of the control device 1a is synchronized with that of the radiography device 2.

5-3. Dynamic Radiography Processing

Next, the dynamic radiography processing shown in FIG. 7, which is executed by the control device 1a, the radiography device 2, and the console 5, will be described. In the mobile radiography system 100A with the timekeeping information of the control device 1a being synchronized with that of the radiography device 2, in response to pressing down of the exposure switch 6a by a user, the dynamic radiography processing is executed.

In the dynamic radiography processing, first, the console 5 sends a radiography start signal to the control device 1a (Step B1).

The radiation-side controller 11 receives the radiography start signal and transmits an exposure permission request to the radiography device 2 (Step B2).

The radiography-side controller 21 receives the exposure permission request and starts generating image data. Then, the radiography-side controller 21 transmits, to the control device 1a, information of N1 (=n1+m) together with notification of permission for exposure (Step B3).

N1 is the sum of:
a count value n1 at the start of generation of image data (the first time point count value); and
a count value m corresponding to the upper limit of the delay time for notification of permission for exposure (the third time point count value).

The upper time limit of the delay time for notification of permission for exposure is preset based on the maximum number of radiographs and the number of possible radiographs.

The radiation-side controller 11 receives the exposure permission notification and the N1 information and determines whether the count value n2 at the time of receipt of the exposure permission notification (the second time point count value) is less than or equal to N1 (Step B4).

In a case where n2 is less than or equal to N1 (YES in Step B4), the radiation-side controller 11 controls the high voltage generator 12 to start exposure (Step B5).

In a case where n2 is greater than N1 (NO in Step B4), the radiation-side controller 11 does not permit exposure (Step B6) and finishes the processing.

Thus, the number of pieces of image data (n2−n1) generated in the delay time for notification of permission for exposure is less than or equal to the count value m corresponding to the upper time limit of delay for notification of permission for exposure. Thus, the sum of the number of possible radiographs and the number of pieces of image data generated during the delay time for notification of permission for exposure is less than or equal to the maximum number of radiographs. Unnecessary exposure is prevented.

After Step B5, the radiation-side controller 11 transmits to the radiography device 2, the n2 information as information at the time point at which radiation is started (Step B7).

The radiography-side controller 21 receives the n2 information and sequentially transmits to the console 5, image data generated after n2 (Step B8).

The console 5 determines whether the exposure switch 6a is released by a user before the number of possible radiographs is finished (Step B9).

In a case where the exposure switch 6a is not released (NO in Step B9), the console 5 proceeds to Step B9 of the processing.

In a case where the exposure switch 6a is released (YES in Step B9), the console 5 sends a radiography stop signal to the control device 1a (Step B10).

The radiation-side controller 11 receives the radiography stop signal and controls the high voltage generator 12 to stop exposure (Step B11).

The radiation-side controller 11 transmits to the radiography device 2, information on the count value n3 at the time of stop of exposure together with the notification of stop of exposure (Step B12).

The radiography-side controller 21 receives the notification of stop of exposure and the n3 information, and finishes generating image data. The radiography-side controller 21 transmits image data generated by n3 to the console 5 (Step B13). The radiography-side controller 21 finishes the processing. The radiography-side controller 21 identifies image data generated between n2 and n3 as exposure image data.

Modification 1

Next, Modification 1 of the embodiment will be described.

Figure 8:
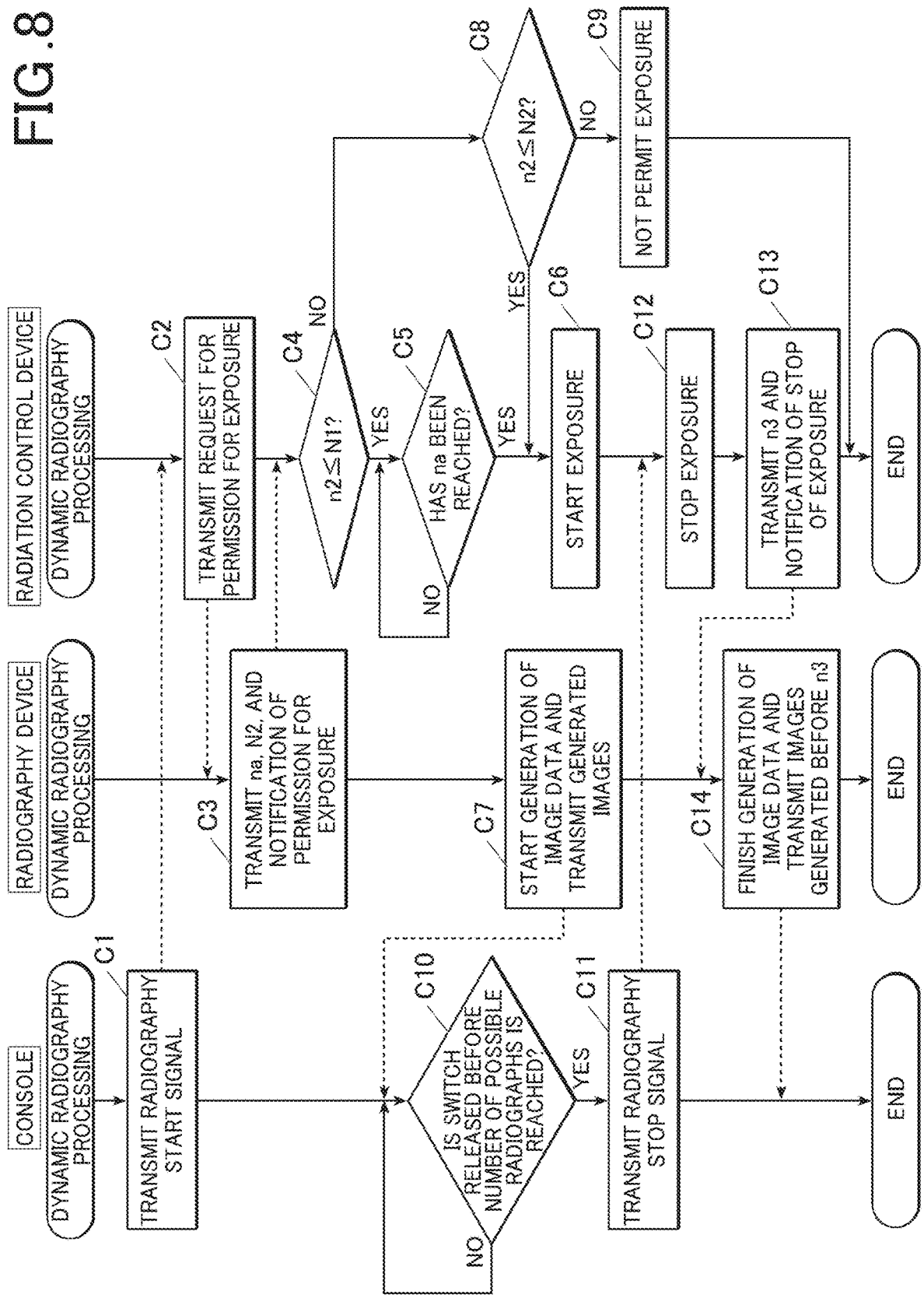
FIG. 8 is a flowchart showing dynamic radiography processing of Modification 1.

FIG. 8 is a flowchart showing dynamic radiography processing of the modification. In the following, we will focus on differences from the above embodiment. The configuration of the mobile radiography system 100A according to the modification is the same as that of the mobile radiography system 100A according to the above embodiment.

In the dynamic radiography processing of the modification shown in FIG. 8, first, the console 5 performs Step C1 which is similar to Step B1 in the dynamic radiography processing of the above embodiment. 1.

The radiation-side controller 11 performs Step C2 which is similar to Step B2 in the dynamic radiography processing of the above embodiment.

The radiography-side controller 21 starts generating image data after a predetermined time. The count value after the predetermined time is na (the fourth time point count value). The predetermined time may be set to, for example, an average value of the delay time for notification of permission for exposure. The radiography-side controller 21 transmits, to the control device 1a, the na information and the N2 (=na+m) information together with the notification of permission for exposure (Step C3). N2 is the sum of na and the count value m corresponding to the upper limit of the delay time for notification of permission for exposure.

The radiation-side controller 11 receives the na information, the N2 information, and the exposure permission notification, and determines whether n2, which is the count value at the time of receipt of the notification of permission for exposure, is less than na (Step C4).

In a case where n2 is less than na (YES in Step C4), the radiation-side controller 11 determines whether the count value has reached na (step C5).

In a case where the count value has not reached na (NO in Step C5), the radiation-side controller 11 proceeds to Step C5 of the processing. Thus, the radiation-side controller 11 waits until the count value reaches na.

When the count value reaches na (YES in Step C5), the radiation-side controller 11 controls the high voltage generator 12 to start exposure (Step C6). At the same time, the radiography-side controller 21 starts generating image data and sequentially transmits the generated image data to the console 5 (Step C7).

In a case where n2 is not less than na (NO in Step C4), the radiation-side controller 11 determines whether n2 is less than or equal to N2 (Step C8).

In a case where n2 is less than or equal to N2 (YES in Step C8), the radiation-side controller 11 proceeds to Step C6 of the processing. In this case, the radiation-side controller 11 transmits to the radiography device 2, the n2 information as information at the time point at which radiation is started. The radiography-side controller 21 receives the n2 information and sequentially transmits to the console 5, image data generated after n2, instead of Step C7.

In a case where n2 is greater than N2 (NO in Step C8), the radiation-side controller 11 does not permit exposure (Step C9) and finishes the processing.

After Step C7, the console 5 performs Steps C10-C11 which are similar to Steps B9-B10 in the dynamic radiography processing of the above embodiment.

The radiation-side controller 11 performs Steps C12-C13 which are similar to Steps B11-B12 in the dynamic radiography processing of the above embodiment.

The radiography-side controller 21 performs Step C14 which is similar to Step B13 in the dynamic radiography processing of the above embodiment and finishes the processing.

The radiography-side controller 21 identifies, as the exposure image data, image data generated between na and n3 (in a case of n2<na) or between n2 and n3 (in a case of n2>na).

In the dynamic radiography processing of Modification 1, in a case where n2 is less than na, non-exposure image data can be prevented from being generated during the delay time for notification of permission for exposure.

Modification 2

Next, Modification 2 of the above embodiment will be described.

Figure 9:
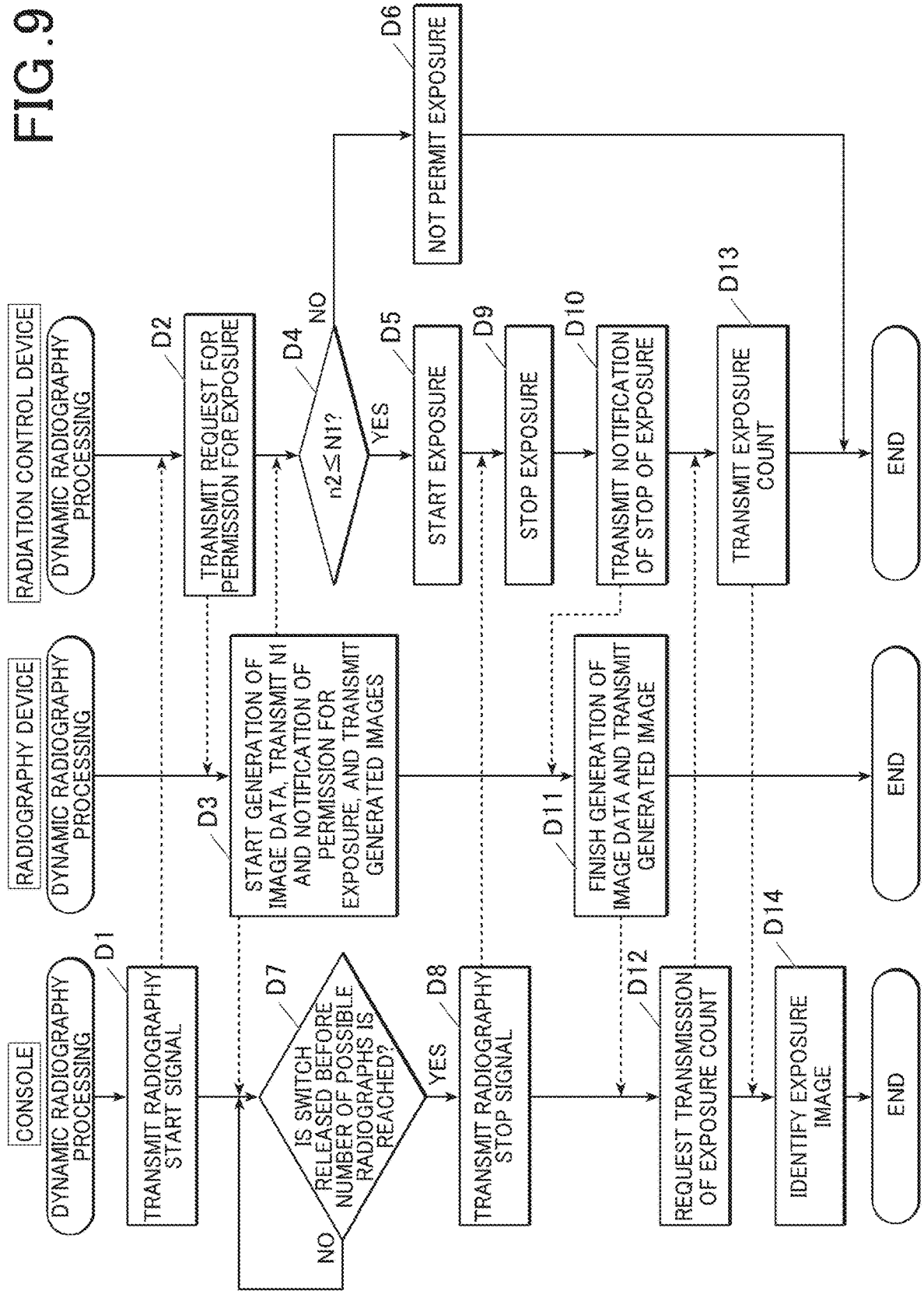
FIG. 9 is a flowchart showing dynamic radiography processing of Modification 2.

FIG. 9 is a flowchart showing the dynamic radiography processing of the modification. In the following, we will focus on differences from the above embodiment. The configuration of the mobile radiography system 100A according to the modification is the same as that of the mobile radiography system 100A according to the above embodiment.

In the dynamic radiography processing of the modification, the console 5 identifies exposure image data after generation of image data is completed.

In the dynamic radiography processing of the modification shown in FIG. 9, first, the console 5 performs Step D1 which is similar to Step B1 in the dynamic radiography processing of the above embodiment.

The radiation-side controller 11 performs Step D2 which is similar to Step B2 in the dynamic radiography processing of the above embodiment.

The radiography-side controller 21 starts generating image data. The radiography-side controller 21 transmits, to the control device 1a, the N1 (=n1+m) information together with the exposure permission notification.

N1 is the sum of:
 the count value n1 at the start of generation of image data; and
 the count value m corresponding to the upper limit of the delay time for notification of permission for exposure.

The radiography-side controller 21 sequentially transmits the generated image data to the console 5 (Step D3).

The radiation-side controller 11 performs Steps D4-D6 which are similar to Steps B4-B6 in the dynamic radiography processing of the above embodiment.

The console 5 performs Steps D7-D8 which are similar to Steps B9-B10 in the dynamic radiography processing of the above embodiment.

The radiation-side controller 11 performs Step D9, which is similar to Step B11 in the dynamic radiography processing of the above embodiment.

The radiation-side controller 11 transmits an exposure stop notification to the radiography device 2 (Step D10).

The radiography-side controller 21 receives the exposure stop notification and finishes generation of image data. The radiography-side controller 21 transmits generated image data to the console 5 (Step D11).

The console 5 transmits, to the control device 1a, request for transmission of a range of count value in which exposure is performed (Step D12).

The radiation-side controller 11 transmits to the console 5, the range of count value in which exposure is performed (Step D13).

The console 5 identifies exposure image data from pieces of image data transmitted from the radiography device 2 based on the received range of count value in which exposure is performed (Step D14). The console 5 finishes the processing.

Modification 3

Next, Modification 3 of the above embodiment will be described.

Figure 10:
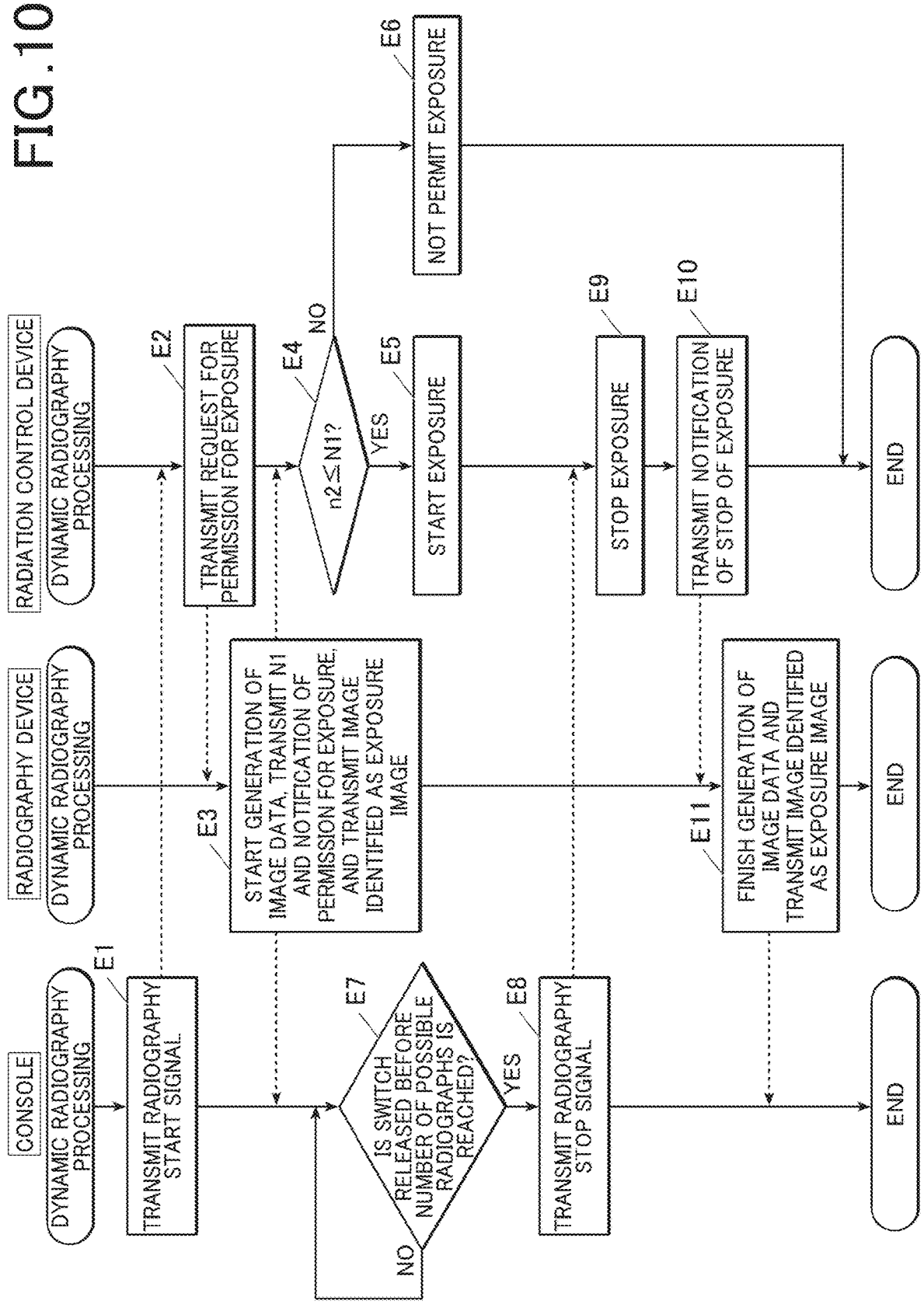
FIG. 10 is a flowchart showing dynamic radiography processing of Modification 3.

FIG. 10 is a flowchart showing the dynamic radiography processing of the modification. In the following, we will focus on differences from the above embodiment.

The radiography system 2 of the mobile radiography system 100A of the modification includes a radiation sensor that detects radiation. The radiography device 2 identifies non-exposure image data and exposure image data according to increase and decrease in detected values by the radiation sensor.

The radiography device 2 may identify non-exposure image data and exposure image data according to increase and decrease in signal values read by the reader 23.

The radiography device 2 may identify non-exposure image data and exposure image data according to shapes in generated image data.

In the dynamic radiography processing of the modification shown in FIG. 10, first, the console 5 performs Step E1 which is similar to Step B1 in the dynamic radiography processing of the above embodiment.

The radiation-side controller 11 performs Step E2 which is similar to Step B2 in the dynamic radiography processing of the above embodiment.

The radiography-side controller 21 starts generating image data. The radiography-side controller 21 transmits, to the control device 1a, the N1 (=n1+m) information together with the exposure permission notification.

N1 is the sum of:
 the count value n1 at the start of generation of image data; and
 the count value m corresponding to the upper limit of the delay time for notification of permission for exposure.

Then, the radiography-side controller 21 sequentially transmits to the console 5, image data identified as exposure image data by the above-mentioned identification method among pieces of generated image data (Step E3).

The radiation-side controller 11 performs Steps E4-E6 which are similar to Steps B4-B6 in the dynamic radiography processing of the above embodiment.

The console 5 performs Steps E7-E8 which are similar to Steps B9-B10 in the dynamic radiography processing of the above embodiment.

The radiation-side controller 11 performs Step E9 which is similar to Step B11 in the dynamic radiography processing of the above embodiment.

The radiation-side controller 11 transmits exposure stop notification to the radiography device 2 (Step E10).

Upon receipt of the exposure stop notification, the radiography-side controller 21 finishes generation of image data. The radiography-side controller 21 transmits to the console 5, image data that is identified as exposure image data by the above-mentioned identification method among pieces of generated image data (Step E11). The radiography-side controller 21 finishes the processing.

Modification 4

Next, Modification 4 of the above embodiment will be described.

FIG. 11 is a flowchart showing dynamic radiography processing of the modification. In the following, we will focus on differences from the above embodiment. The configuration of the mobile radiography system 100A according to the modification is the same as that of the mobile radiography system 100A according to the above embodiment.

In the dynamic radiography processing of the modification, the console 5 sequentially identifies exposure image data among pieces of image data transmitted by radiography device 2.

In the dynamic radiography processing of the modification shown in FIG. 10, first, the console 5 performs Step F1 which is similar to Step B1 in the dynamic radiography processing of the above embodiment.

The radiation-side controller 11 performs Step F2 which is similar to Step B2 in the dynamic radiography processing of the above embodiment.

The radiography-side controller 21 starts generating image data. The radiography-side controller 21 transmits, to the control device 1a, the N1 (=n1+m) information together with the exposure permission notification.

N1 is the sum of:
the count value n1 at the start of generation of image data; and
the count value m corresponding to the upper limit of the delay time for notification of permission for exposure.

The radiography-side controller 21 sequentially transmits generated image data to the console 5 (Step F3).

The console 5 identifies exposure image data among pieces of transmitted image data based on increase/decrease or shape of signal values in the transmitted image data (Step F4).

The radiation-side controller 11 performs Steps F5-F7 which are similar to Steps B4-B6 in the dynamic radiography processing of the above embodiment.

The console 5 performs steps F8-F9 which are similar to Steps B9-B10 in the dynamic radiography processing of the above embodiment.

The radiation-side controller 11 performs Step F10 which is similar to Step B11 in the dynamic radiography processing of the above embodiment.

The radiation-side controller 11 transmits exposure stop notification to the radiography device 2 (Step F11).

The radiography-side controller 21 receives the exposure stop notification and finishes generation of image data. The radiography-side controller 21 transmits generated image data to the console 5 (Step F12).

The console 5 identifies exposure image data among transmitted pieces of image data based on increase/decrease or shape of signal values in the transmitted image data (Step F13). The console 5 finishes the processing.

Modification 5

Next, Modification 5 of the above embodiment will be described.

FIG. 12 is a flowchart showing dynamic radiography processing of the modification. In the following, we will focus on differences from the above embodiment. The configuration of the mobile radiography system 100A according to the modification is the same as that of the mobile radiography system 100A according to the above embodiment.

The dynamic shooting processing of the modification is applied to a case where the number of possible radiographs is finished. This is different from the above embodiment in which the exposure switch 6a is released by a user before the number of possible radiographs is finished.

In the dynamic radiography processing of the modification shown in FIG. 12, first, the console 5 performs Step G1 which is similar to Step B1 in the dynamic radiography processing of the above embodiment.

The radiation-side controller 11 performs Step G2 which is similar to Step B2 in the dynamic radiography processing of the above embodiment.

The radiography-side controller 21 performs Step G3 which is similar to Step B3 in the dynamic radiography processing of the above embodiment.

The radiation-side controller 11 performs Steps G4-G7 which are similar to Steps B4-B7 in the dynamic radiography processing of the above embodiment.

The radiography-side controller 21 performs Step G8 which is similar to Step B8 in the dynamic radiography processing of the above embodiment.

The radiation-side controller 11 determines whether the number of image data generated after n2 in the radiography device 2 has reached the number of possible radiographs (Step G9).

In a case where the number of possible radiographs has not been reached (NO in Step G9), the radiation-side controller 11 proceeds to Step G9 of the processing.

In a case where the number of possible radiographs has been reached (YES in Step G9), the radiation-side controller 11 controls the high voltage generator 12 to stop exposure (Step G10).

After Step G8, the radiography-side controller 21 determines whether the number of images generated after n2 in the radiography device 2 has reached the number of possible radiographs (Step G11).

In a case where the number of possible radiographs has not been reached (NO in Step G11), the radiography-side controller 21 proceeds to Step G11 of the processing.

In a case where the number of possible radiographs has been reached (YES in Step G11), the radiography-side controller 21 finishes generating image data and transmits generated image data to the console 5 (Step G12). The radiography-side controller 21 finishes the processing.

The radiography-side controller 21 identifies image data generated after n2 as exposure image data.

Since the timekeeping information of the control device 1a is synchronized with that of the radiography device 2, stop of exposure in Step G10 and finish of generation of image data in Step G12 in the dynamic radiography processing of the modification are performed simultaneously. This prevents non-exposure image data from being generated during the delay time for notification of stop of exposure.

Modification 6

Next, Modification 6 of the above embodiment will be described.

FIG. 13 is a flowchart showing dynamic radiography processing of the modification. In the following, we will focus on differences from the above embodiment.

The radiography device 2 of the modification includes the first notification unit (not shown) that notifies a user with light, sound, vibration, etc. The console 5 includes the second notification unit (not shown) that notifies a user with light, sound, vibration, etc.

Figure 7:
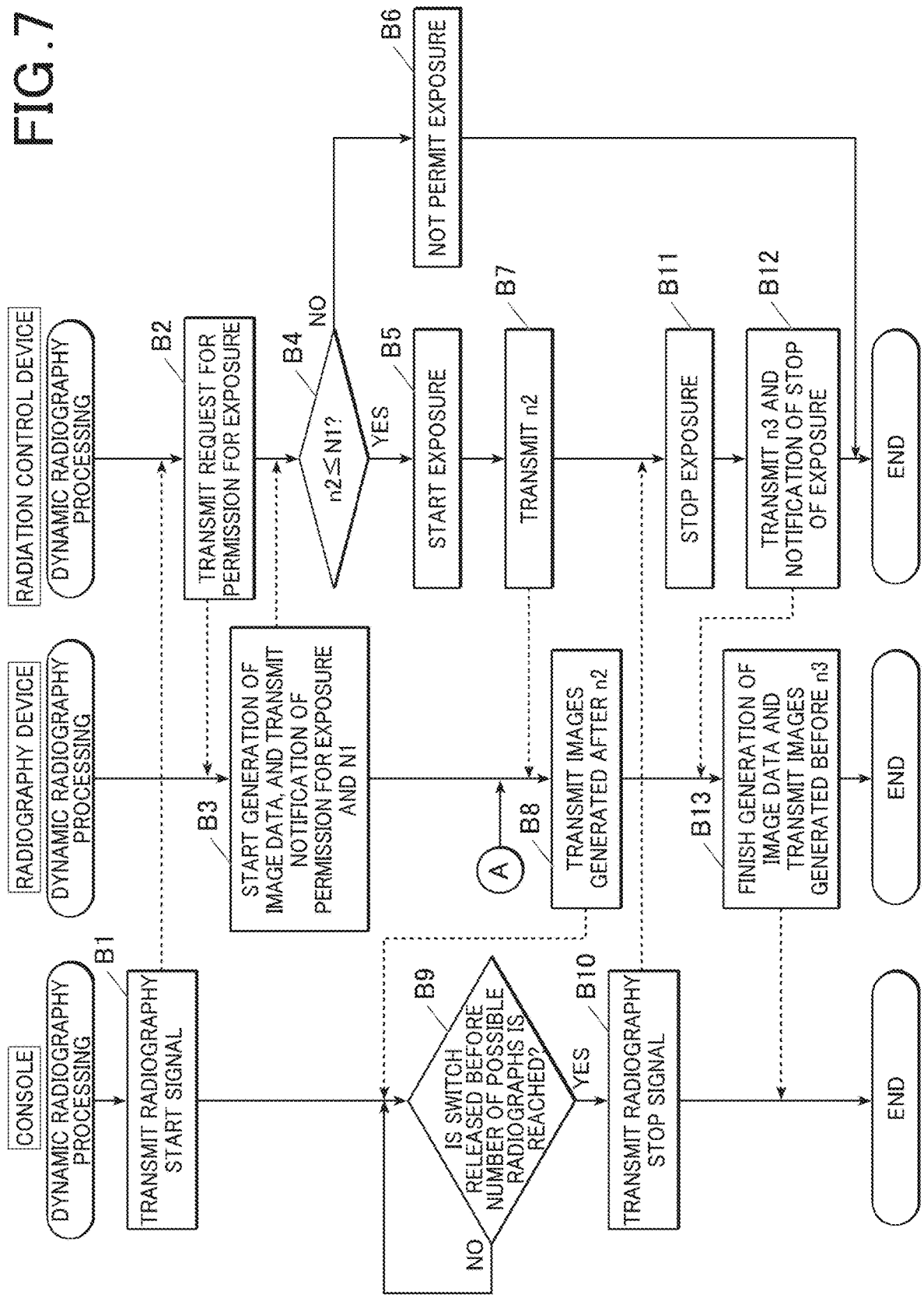
FIG. 7 is a flowchart showing dynamic radiography processing.

The dynamic radiography processing in this modification is applied to a case where:
in the dynamic radiography processing of the embodiment shown in FIG. 7, due to communication failure, etc. between the control device 1a and the radiography device 2 after Step B3, communication between the control device 1a and the radiography device 2 becomes impossible; and
the number of possible radiographs is finished before a user releases the exposure switch 6a.

In the dynamic radiography processing of the modification shown in FIG. 13, first, the console 5 performs Step H1 which is similar to Step B1 in the dynamic radiography processing of the above embodiment.

The radiation-side controller 11 performs Step H2 which is similar to Step B2 in the dynamic radiography processing of the above embodiment.

The radiography-side controller 21 performs Step H3 which is similar to Step B3 in the dynamic radiography processing of the above embodiment.

The radiation-side controller 11 performs Steps H4-H7 which is similar to Steps B4-B7 in the dynamic radiography processing of the above embodiment.

The radiation-side controller 11 determines whether the number of image data generated after n2 in the radiography device 2 has reached the number of possible radiographs (Step H8).

In a case where the number of possible radiographs has not been reached (NO in Step H8), the radiation-side controller 11 proceeds to Step H8 of the processing.

In a case where the number of possible radiographs has been reached (YES in Step H8), the radiation-side controller 11 controls the high voltage generator 12 to stop exposure (Step H9).

After Step H3, the radiography-side controller 21 determines whether the n2 information has been received from the control device 1a (Step H10).

As shown in FIG. 7, when communication is possible between the control device 1a and the radiography device 2, and the radiography-side controller 21 receives the n2 information (YES in Step H10), the radiography-side controller 21 proceeds to Step B8 of the processing in FIG. 7. Thus, the radiography-side controller 21 sequentially transmits to the console 5, image data generated after n2.

In a case where the n2 information is not received (NO in Step H10), the radiography-side controller 21 determines whether the count value has reached N1 (Step H11).

In a case where the count value has not reached N1 (NO in Step H11), the radiography-side controller 21 proceeds to Step H10 of the processing. Thus, the radiography-side controller 21 waits for the n2 information to be received until the count value reaches N1. This is because the n2 information, as information of a time point at which radiation is started, may be transmitted to the radiography device 2 from the radiation-side controller 11 before N1.

In a case where the count value reaches N1 (YES in Step H11), the radiography-side controller 21 sequentially transmits to the console 5, image data generated after n1 together with information that image data generated after n1 includes non-exposure image data (Step H12). Image data generated after n1 includes non-exposure image data because communication between the control device 1a and the radiography device 2 becomes impossible. The radiography-side controller 21 is unable to obtain count values in which exposure is performed, and exposure image data cannot be identified.

Thus, in Steps H10-H11, the radiography-side controller 21 determines whether information (n2) at the time point at which the radiation device 1 starts radiation is received within a predetermined period (before the count value reaches N1). Thus, the radiography-side controller 21 functions as the second determiner.

In a case where the second determiner determines that the information at the time point at which radiation is started is received within the predetermined period, the radiography-side controller 21 transmits to a predetermined external device such as the console 5, dynamic image data generated after the time point (n2) at which radiation is started.

In a case where the second determiner determines that the information at the time point at which radiation is started is not received within the predetermined period, in Step H12, the radiography-side controller 21 transmits to a predetermined device such as the console 5:
dynamic image data generated after the time point (n1) at which generation of dynamic image data is started; and
information that dynamic image data to be transmitted includes non-exposure image data.

Thus, the radiography-side controller 21 functions as the third transmitter.

Next, the radiography-side controller 21 determines whether image data generated by the radiography device 2 after start of generation of image data (after n1) has reached the maximum number of radiographs (Step H13).

In a case where the maximum number of radiographs has not been reached (NO in Step H13), the radiography-side controller 21 proceeds to Step H13 of the processing.

In a case where the maximum number of radiographs has been reached (YES in Step H13), the radiography-side controller 21 finishes generation of image data. The radiography-side controller 21 sends to the console 5, the generated image data with information that the image data includes non-exposure image data (Step H14).

The radiography-side controller 21 controls the first notification unit to perform notification indicating that the transmitted image data includes non-exposure image data (Step H15).

The console 5 receives the image data and the information that the image data includes non-exposure image data. The console 5 controls the second notification unit to perform notification indicating that the image data includes non-exposure image data (Step H16).

The console 5 transmits, to the control device 1a, request for transmission of a range of count value in which exposure is performed (Step H17).

The radiation-side controller 11 transmits to the console 5, the range of count value in which exposure is performed (Step H18).

The console 5 identifies exposure image data from pieces of image data transmitted from the radiography device 2 based on the received range of count value in which exposure is performed (Step H19). The console 5 finishes the processing.

In steps H15 and H16 of Modification 6, the notification indicating that the image data includes non-exposure image data prompts a user to check images and delete the non-exposure image.

The radiography device 2 of the embodiment, Modification 1, Modification 3, and Modification 5 may include the first notification unit similar to Modification 6. In the embodiment, Modification 1, Modification 3, and Modification 5, the radiography-side controller 21 identifies exposure image data. The first identification unit of the radiography-side controller 21 may determine whether exposure image data is identified. Thus, the radiography-side controller 21 functions as the first identification determiner. The radiography-side controller 21 transmits result of determination by the first notification determiner to a predetermined external device (e.g., the console 5). Thus, the radiography-side controller 21 functions as the second transmitter. The radiography-side controller 21 controls the first notification unit to perform notification indicating the result of determination by the first identification determiner. Thus, the radiography-side controller 21 functions as the first notification unit.

The console 5 may have the second notification unit similar to Modification 6. The console 5 receives the determination result transmitted from the radiography device 2, which concerns whether exposure image data has been identified in the radiography device 2. The console 5 controls the second notification unit to perform notification indicating the determination result.

Other devices such as the control device 1a may include the notification unit. The radiography-side controller 21 transmits the result of determination by the first identification determiner to another device. The other device receives the determination result and controls the notification unit to perform notification indicating the determination result.

In Modification 2, Modification 4 and Modification 6, the console 5 identifies exposure image data. The second identification unit of the console 5 may determine whether exposure image data is identified. Thus, the console 5 functions as the second identification determiner. The console 5 controls the second notification unit to perform notification indicating the result of determination by the second identification determiner. Thus, the console 5 functions as the second notification unit.

Advantageous Effect

The radiography system 100 (mobile radiography system 100A) described above is wirelessly connected to the radiography device 2 that generates dynamic image data and controls sequential radiation to a subject.

The radiation device includes:
a signal generator (radiation-side controller 11) that generates:
the first pulse signals emitted by the radiography device;
the second pulse signals synchronized with the first count value obtained by counting up the first pulse signals; and
the second count value obtained by counting up the second pulse signals.

The first determiner (radiation-side controller 11) determines whether to start radiation based on a delay time which is a difference between:
the first time point count value (n1) indicating a time point at which a radiation permission signal is transmitted; and
a second time point count value (n2) indicating a time point at which the radiation permission signal is received.

The radiation permission signal is wirelessly transmitted from the radiography device to allow the radiation device to start radiation.

Therefore, even when the radiation device that generates radiation and the radiography device that generates radiation images are wirelessly connected, the first determiner can determine whether the communication status is fine or not. This allows for better dynamic radiography that produces multiple frame images.

In the radiation device, the first determiner determines to start radiation when the second time point count value is less than or equal to the sum of:
the first time point count value; and
the third time point count value (m) corresponding to the maximum time between the time when the radiography device starts generating dynamic image data and the time when the radiation device starts radiation.

This prevents unnecessary exposure in which exposure occurs while image data cannot be generated.

In the radiation device, the first determiner determines which of the fourth time point count value (na) and the second time point count value is greater. The fourth time point count value indicates a time point at which the radiography device starts generating dynamic image data in response to wireless transmission of the radiation permission signal from the radiography device. In a case where the fourth time point count value is greater than the second time point count value, the first determiner determines to start radiation when the second time point count value reaches the fourth time point count value.

Therefore, in a case where n2 is less than na, non-exposure image data can be prevented from being generated during the delay time for notification of permission for exposure.

The radiation device includes the first transmitter (radiation-side controller 11) that transmits, to a predetermined external device, information on a time point at which radiation is started.

Therefore, exposure image data is identified based on the information on the time point at which radiation is started.

The radiography device that is connected to the radiation device includes the first identification unit (radiography-side controller 21). The first identification unit identifies exposure image data generated under radiation among generated pieces of dynamic image data based on information on a time point at which radiation is started.

Since the radiography device identifies exposure image data, non-exposure image data can be, for example, deleted.

The radiography device includes:
the first notification unit that performs notification with light, sound, or vibration;
the first identification determiner (radiography-side controller 21) that determines whether exposure image data has been identified by the first identification unit; and
the first notification controller (radiography-side controller 21) that makes the first notification unit perform notification based on result of determination by the first identification determiner.

Therefore, when the radiography-side controller 21 cannot identify exposure image data, notification to a user prompts the user to check images and delete non-exposure images.

The radiography device includes the second transmitter (radiography-side controller 21) that transmits, to a predetermined external device, result of determination by the first identification determiner.

Therefore, when the radiography-side controller 21 cannot identify exposure image data, the radiography device can send this information to an external device to prompt a user to check images and delete non-exposure image.

The radiography device 2 is wirelessly connected to the radiation device 1 and generates dynamic image data. The radiation device controls sequential radiation to a subject.

The radiography device includes:
the second determiner (radiography-side controller 21) that determines whether information on a time point at which the radiation device starts radiation is received within a predetermined period; and
the third transmitter (radiography-side controller 21).

In a case where the second determiner determines that information on a time point at which radiation is started is received within the predetermined period, the third transmitter transmits, to a predetermined external device, dynamic image data generated after the time point at which radiation is started.

In a case where the second determiner determines that information on a time point at which radiation is started is not received within the predetermined period, the third transmitter transmits, to a predetermined external device:
dynamic image data generated after a time point at which generation of dynamic image data is started; and
information that dynamic image data includes non-exposure image data.

Therefore, in a case where the radiography-side controller 21 cannot identify exposure image data because it cannot obtain information on a time point at which radiation is started, a predetermined external device, such as a console, identifies exposure image data.

Radiography device can be stored in a medical vehicle and is portable.

Therefore, it is possible to perform radiography without communication cables.

The second identification unit (console 5) is connected with the radiation device. The console 5 identifies exposure image data generated under radiation among pieces of dynamic image data based on increase/decrease or shape of signal values in dynamic image data transmitted from the radiography device.

Since the console 5 identifies exposure image data, non-exposure image data can be, for example, deleted.

The console 5 includes:
the second notification unit that performs notification with light, sound, or vibration;
the second identification unit (console 5) that determines whether the exposure image data has been identified by the second identification unit; and
the second notification controller (console 5) that makes the second notification unit perform notification based on result of determination by the second identification determiner.

Therefore, in a case where the console 5 cannot identify exposure image data, notification to a user prompts the user to check images and delete non-exposure images.

In the console 5, the second notification controller makes the second notification unit perform notification based on determination result which concerns whether the radiography device has identified exposure image data, and which is transmitted from the radiography device.

Therefore, when the radiography device 2 cannot identify exposure image data, notification to a user prompts the user to check images and delete non-exposure images.

The above embodiment is one preferable example of a radiography system according to the present invention. The present invention is not limited to this.

For example, in the dynamic radiography processing of the embodiment, the radiography-side controller 21 transmits to the console 5, image data generated between n2 and n3. The present invention is not limited to this. Information of exposure image data may be associated with image data generated between n2 and n3. Also, image data generated before n2, and image data generated after n3 may be associated with information of non-exposure image data. They are transmitted to the console 5. In the console 5, only the image data associated with information of exposure image data may be displayed. The present invention may have configuration to set switching of these operations.

In the dynamic radiography processing of the embodiment and modifications, the radiation device, and the radiography device of the radiography system 100 are wirelessly connected. The present invention is not limited to this. Even in a radiography system in which a radiation device and a radiography device are connected by a cable or other wired connection, the above embodiment and modifications can be performed. Dynamic radiography that generates multiple frame images can be performed more suitably.

Detailed configuration and detailed operation of devices constituting the radiography system 100 may also be modified within the scope of the claims of the invention.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese patent application No. 2021-103357, filed on Jun. 22, 2021, is incorporated herein by reference in its entirety.

What is claimed is:

1. A radiation device which is wirelessly connected to a radiography device that generates dynamic image data and which controls sequential radiation to a subject, the radiation device comprising:
   a signal generator; and
   a first determiner,
   wherein
   the signal generator generates:
      first pulse signals emitted by the radiography device,
      second pulse signals synchronized with a first count value obtained by counting up the first pulse signals; and
      a second count value obtained by counting up the second pulse signals, and
   the first determiner determines whether to start radiation based on a delay time which is a difference between:
      a first time point count value indicating a time point at which a radiation permission signal is transmitted, the radiation permission signal being wirelessly transmitted from the radiography device to allow the radiation device to start radiation; and
      a second time point count value indicating a time point at which the radiation permission signal is received.

2. The radiation device according to claim 1, wherein:
   the first determiner determines to start radiation in a case where the second time point count value is less than or equal to a sum of the first time point count value and a third time point count value, and
   the third time point count value corresponds to an upper limit of time between start of generation of dynamic image data by the radiography device and start of radiation by the radiation device.

3. The radiation device according to claim 1, wherein:
   the first determiner determines which of the second time point count value and a fourth time point count value is greater, the fourth time point count value indicating a time point at which the radiography device starts generating the dynamic image data in response to wireless transmission of the radiation permission signal from the radiography device, and
   in a case where the fourth time point count value is greater than the second time point count value, the first determiner determines to start radiation when the second time point count value reaches the fourth time point count value.

4. The radiation device according to claim 1, further comprising:
   a first transmitter that transmits, to a predetermined external device, information on a time point at which radiation is started.

5. The radiography device connected to the radiation device according to claim 4, the radiation device comprising:
   a first identification unit that identifies exposure image data generated under radiation among generated pieces of the dynamic image data based on the information on the time point at which radiation is started.

6. The radiography device according to claim 5, further comprising:
a first notification unit that performs notification with light, sound, or vibration,
a first identification unit that determines whether the first identification unit has identified the exposure image data; and
a first notification controller that makes the first notification unit perform notification based on result of determination by the first identification determiner.

7. The radiography device according to claim 6, further comprising:
a second transmitter that transmits, to a predetermined external device, result of determination by the first identification determiner.

8. The radiography device according to claim 5 which is configured to be stored in a medical vehicle and which is portable.

9. A console that is configured to be connected with the radiation device according to claim 1, the console comprising:
a second identification unit that identifies exposure image data generated under radiation among pieces of the dynamic image data based on increase/decrease or shape of signal values in the dynamic image data transmitted from the radiography device.

10. The console according to claim 9 comprising:
a second notification unit that performs notification with light, sound, or vibration,
a second identification determiner that determines whether the second identification unit has identified the exposure image data; and
the second notification controller that makes the second notification unit perform notification based on result of determination by the second identification determiner.

11. The console according to claim 10, wherein:
the second notification controller makes the second notification unit perform notification based on determination result of determining whether the exposure image data has been identified in the radiography device, the determination result being transmitted from the radiography device.

12. A radiography device which generates dynamic image data, and which is wirelessly connected to a radiation device that controls sequential radiation to a subject, the radiography device comprising:

a second determiner that determines whether information on a time point at which the radiation device starts radiation is received within a predetermined period; and
a third transmitter,
wherein
in a case where the second determiner determines that the information on the time point at which radiation is started is received within the predetermined period, the third transmitter transmits, to a predetermined external device, the dynamic image data generated after the time point at which radiation is started, and
in a case where the second determiner determines that the information on the time point at which radiation is started is not received within the predetermined period, the third transmitter transmits, to a predetermined external device,
the dynamic image data generated after a time point at which generation of the dynamic image data is started; and
information that the dynamic image data includes non-exposure image data.

13. A non-transitory computer-readable recording medium storing a program for a computer of a radiation device, wherein:
the radiation device controls sequential radiation to a subject and is wirelessly connected to a radiography device that generates dynamic image data,
the program makes the computer function as:
a signal generator; and
a first determiner,
the signal generator generates:
first pulse signals emitted by the radiography device,
second pulse signals synchronized with a first count value obtained by counting up the first pulse signals; and
a second count value obtained by counting up the second pulse signals, and
the first determiner determines whether to start radiation based on a delay time which is a difference between:
a first time point count value indicating a time point at which a radiation permission signal is transmitted, the radiation permission signal being wirelessly transmitted from the radiography device to allow the radiation device to start radiation; and
a second time point count value indicating a time point at which the radiation permission signal is received.

\* \* \* \* \*